(12) United States Patent
Blick

(10) Patent No.: US 9,819,305 B2
(45) Date of Patent: Nov. 14, 2017

(54) KIT FOR CONVERTING A BATTERY-POWERED AUTOMATIC FRAGRANCE SPRAYER TO SOLAR POWER

(71) Applicant: Vivian Blick, Gloucester (GB)

(72) Inventor: Vivian Blick, Gloucester (GB)

(73) Assignee: Vivian Blick, Gloucester (GB)

( * ) Notice: Subject to any disclaimer, the term of this patent is extended or adjusted under 35 U.S.C. 154(b) by 118 days.

(21) Appl. No.: 14/915,500

(22) PCT Filed: Aug. 29, 2014

(86) PCT No.: PCT/GB2014/052628
§ 371 (c)(1),
(2) Date: Feb. 29, 2016

(87) PCT Pub. No.: WO2015/028816
PCT Pub. Date: Mar. 5, 2015

(65) Prior Publication Data
US 2016/0211799 A1    Jul. 21, 2016

(30) Foreign Application Priority Data

Aug. 29, 2013  (GB) .................................. 1315357.2
May 13, 2014  (GB) .................................. 1408486.7

(51) Int. Cl.
*H02S 40/38* (2014.01)
*A61L 9/14* (2006.01)

(52) U.S. Cl.
CPC ................ *H02S 40/38* (2014.12); *A61L 9/14* (2013.01)

(58) Field of Classification Search
None
See application file for complete search history.

(56) References Cited

U.S. PATENT DOCUMENTS

| 5,884,808 A | 3/1999 | Muderlak et al. |
| 5,908,140 A | 6/1999 | Muderlak et al. |

(Continued)

FOREIGN PATENT DOCUMENTS

| CN | 201223841 Y | 4/2009 |
| CN | 201371691 Y | 12/2009 |

(Continued)

OTHER PUBLICATIONS

Combined Search and Examination Report, Great Britain Patent Application No. GB1408486.7, dated Nov. 10, 2014.

(Continued)

*Primary Examiner* — Stephen W Jackson
*Assistant Examiner* — David M Stables
(74) *Attorney, Agent, or Firm* — Marshall, Gerstein & Borun LLP

(57) ABSTRACT

A kit for converting a battery-powered fragrance sprayer of the type described into a solar powered automatic fragrance sprayer for use in an indoor lit area, comprising: a battery pack (24) for fitting into a battery compartment (28) of the fragrance sprayer, the battery pack (24) including a rechargeable nickel-hydride (Ni-Mh) low self-discharge (LSD) battery (30) mounted within a battery casing having positive and negative connection areas (26, 34) at the respective ends for connection with connectors in the battery compartment (28); a replacement outer casing (12) for the fragrance sprayer; at least one tuned amorphous silicon solar panel (14, 16) or at least one dye sensitized solar cell panel (14,16) disposed on the replacement outer casing (12); and cable connection means (32) electrically connecting the at least one tuned amorphous silicon solar panel (14,16) or the at least one dye sensitized solar cell panel (14,16) to the Ni-Mh LSD battery (30) in the battery pack (24).

19 Claims, 2 Drawing Sheets

(56) References Cited

U.S. PATENT DOCUMENTS

| | | |
|---|---|---|
| 2006/0188238 A1 | 8/2006 | Kent |
| 2010/0059602 A1 | 3/2010 | Chiou et al. |
| 2011/0073151 A1 | 3/2011 | Yago |
| 2011/0259973 A1 | 10/2011 | Pedicano et al. |
| 2012/0222935 A1* | 9/2012 | MacKay ............... G07F 17/248 194/210 |
| 2014/0253336 A1* | 9/2014 | Ophardt ............... A47K 5/1202 340/573.1 |

FOREIGN PATENT DOCUMENTS

| | | |
|---|---|---|
| CN | 201453718 U | 5/2010 |
| CN | 201814897 U | 5/2011 |
| EP | 0848999 A2 | 6/1998 |
| EP | 2572969 A1 | 3/2013 |
| KR | 20110029463 A | 3/2011 |
| WO | WO-95/29106 A1 | 11/1995 |

OTHER PUBLICATIONS

Combined Search and Examination Report, Great Britain Patent Application No. GB1315357.2, dated Feb. 28, 2014.
European Examination Report, European Patent Application No. 14758633.3, dated Mar. 17, 2016.
International Preliminary Report on Patentability, International Application No. PCT/GB2014/052628, dated Mar. 1, 2016.
International Search Report and Written Opinion, International Application No. PCT/GB2014/052628, dated Dec. 11, 2014.

* cited by examiner

KIT FOR CONVERTING A BATTERY-POWERED AUTOMATIC FRAGRANCE SPRAYER TO SOLAR POWER

The present invention relates to a kit for converting a battery-powered automatic fragrance sprayer into a solar powered automatic fragrance sprayer for use in an indoor lit area.

BACKGROUND TO THE INVENTION

Automatic fragrance sprayers are widely installed in public toilets, changing rooms, and other spaces where odour may be a problem. These sprayers typically include a timer, and an actuator for releasing a quantity of fragrance from an aerosol. The timer causes the actuator to spray the fragrance at regular intervals. The device is used to control odour in the space in which it is installed.

Typically, the timer and actuator are electrically operated, and are powered by dry cell batteries. These batteries need to be checked on a regular basis, and replaced when they become depleted. This results in an extra task for a janitor to regularly complete. Also, the units are often installed in moist environments, and moisture can cause the batteries to deteriorate and leak, causing damage to the fragrance sprayer itself. Since the batteries must be easily replaceable, it is difficult to protect them from moisture.

Depleted batteries should ideally be recycled to recover raw materials. However, the cost and inconvenience of doing so often means that they are simply discarded with general waste. This is damaging to the environment.

A fragrance sprayer "including a controller, an actuator and an aerosol cannister the controller being adapted to activate the actuator to release fragrance from the aerosol cannister, the fragrance sprayer further comprising at least one cell for powering the controller and actuator" is henceforth referred to as "of the type described".

Mains-powered fragrance sprayers solve the problems of battery replacement. However, they are difficult and costly to install due to the wiring required. An electrician will usually be needed. In contrast, a battery-powered sprayer may simply be fixed to a wall with, for example, screws. A caretaker or in-house handyman will often be able to complete this task in a relatively short period of time, making installation inexpensive. As a result, mains-powered fragrance sprayers are not as commonly used.

Non-electrical automatic fragrance-sprayers are available. Some designs, for example, rely on a hydrogen-generating fuel cell to create gas to continually force fragrance out of a container. However, these devices rely on the passive movement of air to disperse the fragrance (i.e. passive diffusion), rather than actively spraying it into the room. As a result, odour control is not as effective.

It is an object of the invention to provide a fragrance sprayer which reduces or substantially obviates the above mentioned problems.

STATEMENT OF INVENTION

According to the present invention, there is provided a kit for converting a battery-powered automatic fragrance sprayer of the type described into a solar powered automatic fragrance sprayer for use in an indoor lit area, comprising a battery pack for fitting into a battery compartment of the fragrance sprayer, the battery pack including a rechargeable nickel-hydride (Ni-Mh) low self-discharge (LSD) battery mounted within a battery casing having positive and negative connection areas at the respective ends for connection with connectors in the battery compartment; a replacement outer casing for the fragrance sprayer; at least one tuned amorphous silicon solar panel or at least one dye sensitised solar cell panel disposed on the replacement outer casing; and cable connection means electrically connecting the at least one tuned amorphous silicon solar panel or the at least one dye sensitised solar cell panel to the Ni-Mh LSD battery in the battery pack.

The kit is highly advantageous because it enables existing fragrance sprayers to be quickly and easily upgraded to use a more efficient battery and a solar panel(s) in a matter of seconds. It also allows the fragrance sprayer to operate for extended periods without battery maintenance. Significantly, the kit allows the harvesting of light from artificial light sources, which is particularly advantageous in washrooms that are not substantially internally lit by sunlight for much of the day (or at all). The use of a rechargeable nickel hydride low self-discharge battery means that the battery pack generates an electrical voltage through purely chemical means, and does not waste energy powering internal battery functions, further extending its operational time during non-lit periods, if a washroom is closed during the night or over a weekend for example.

Additionally, tuned amorphous silicon solar panels and dye sensitised solar cell panels are found to be ideal for use in the low-light conditions typically found in toilets and washrooms. In particular, they generate a useful amount of power from an artificial light source, as they can be designed specifically to work with high efficiency in a particular spectrum, whether visible light or ultraviolet light, or a combination of both.

The total surface area of the at least one tuned amorphous silicon solar panel or the at least one dye sensitised solar cell may be substantially 80 square centimeters. Preferably, at least one tuned amorphous silicon solar panel or at least one dye sensitised solar cell may harvest energy at a rate of substantially 5 microwatts ($\mu$W) per square centimeter under artificial light conditions of substantially 200 lux.

This ensures that a large area of light-absorbing surface is available to convert photons to electrical energy, overcoming the challenge of operating from the low light intensity produced by ambient room lighting such as fluorescent tubing, for example. The advantages of using at least one dye sensitised solar cell (DSSC) panel to charge the battery pack include the ability of DSSCs to function in low-light conditions, such as the typical light intensity of 200 lux found in washrooms, particularly as they can be designed specifically to work with high efficiency in a particular spectrum. They are also capable of efficiently harvesting light entering from a wide ranges of angles, and particularly acute angles, due to high light penetration into the titanium dioxide nanostructure inside DSSCs. This makes DSSCs ideal for capturing the diffuse light available indoors. Additionally, as they utilise thin-film technology, they do not require a glass substrate and are consequently more robust and flexible.

At least one tuned amorphous silicon solar panel or at least one dye sensitised solar cell panel may be front-mounted and may be disposed substantially vertically when a rear wall of the fragrance sprayer is mounted to a vertical wall.

Placing a solar panel on the front of the fragrance sprayer maximises the degree to which the panel absorbs incident sunlight from any windows, whilst still absorbing an appreciable amount of ambient light from ceiling-mounted lights. Mounting the panel substantially vertically reduces the degree to which it protrudes into the room, reducing the likelihood of damage through a collision.

At least one tuned amorphous silicon solar panel or at least one dye sensitised solar cell panel may be top-mounted and may be disposed substantially at an angle of between 45° and the horizontal when a rear wall of the fragrance sprayer is mounted to a vertical wall, and preferably at an angle of 30° to the horizontal, and more preferably around 20° to the horizontal.

Placing a solar panel on the top of the fragrance sprayer maximises the degree to which the panel absorbs ambient light from the ceiling-mounted lights, whilst still absorbing an appreciable amount of sunlight from any windows.

There may be both front-mounted and top-mounted tuned amorphous silicon solar panels or dye sensitised solar cell panels.

This maximises the surface area of the unit dedicated to harvesting light, and with a greater potential to harvest energy, the unit can function for longer during periods of darkness prior to running out of energy. As such, odours are much less likely to build up in washrooms during periods of non-use. It also means that any defects in one panel do not prevent the fragrance sprayer from functioning, and supports the operation of more frequent fragrance dispersal as available energy is much less of a limiting factor.

The replacement outer casing may include an aperture for the LCD screen and cover the controller. Preferably, the LCD screen may display information relating to the energy level remaining in the battery pack which can be viewed from the aperture. Furthermore, the LCD screen may display information relating to the amount of fragrance remaining which can be viewed from the aperture.

The use of an aperture for the LCD screen allows a user to quickly determine the operative state of the fragrance sprayer. Showing information which informs the user of the energy storage state of the battery permits a quick determination of whether then unit is functioning within normal parameters. With additional information concerning the amount of fragrance left in the aerosol cannister, the user is able to fully assess whether the unit needs to be serviced. Small LCD screens also require minimal power, reducing power usage from the battery. Covering the controller protects it from exposure to moisture and prevents the operating parameters of the fragrance sprayer from being inadvertently changed.

The LCD screen and controller may operate on substantially 10 μA.

By using minimal power to operate the LCD screen and controller, the energy remaining in the battery diminishes less quickly when the fragrance sprayer is operating in unlit conditions, such as through the night or during a weekend. This means that it is less likely to fully deplete its energy supply and cease operating. In fact, the battery has enough reserve for over one month of operation in the absence of any light source (where initially fully charged), with the low current required for the LCD screen and controller as a contributing factor in its longevity.

The kit may be fitted to a battery-powered fragrance sprayer of the type described, in which the fragrance sprayer may include an aerosol cannister with an actuator to release fragrance. The energy delivered by the battery to the actuator may be substantially 0.4 Joules.

By using an aerosol cannister, less energy is needed from the rechargeable cell in dispersing the fragrance because it is pressurised. This reduces the energy requirements of the actuator substantially, and prolongs the life of the battery.

A timer may be included in the battery-powered fragrance sprayer of the type described, and the controller may be adapted to activate the actuator to release fragrance at predetermined time intervals.

The timer allows for regular automatic dispersal of fragrance, ensuring that odours do not accumulate. The fragrance release is advantageously controlled by the electronic actuator, meaning that the fragrance sprayer can operate for long periods of time without relying on user interaction to maintain an odour-free washroom.

The predetermined time interval may be around seven minutes.

It is found that, in typical bathroom lighting conditions, a solar panel in a fragrance sprayer of the type described is able to harvest enough energy for continuous operation at this time interval. This also maintains odour-free conditions without wasting fragrance.

A watertight seal may be introduced in the battery-powered automatic fragrance sprayer of the type described to protect the battery pack from moisture.

If the electronic controller or battery pack were to become wet, their function may become impaired, either by short-circuiting or by gradual chemical degradation (e.g. rusting) in the long term. By providing a watertight seal, this problem is substantially mitigated, as both water vapour and liquid water are prevented from diffusing or dripping into the electrical components. Notably, because the rechargeable cell has a long, maintenance-free life, it may be sealed inside the casing of the sprayer. Although it is envisaged that the battery will eventually need to be changed, the frequency with which this will become necessary will be very low, once every ten years for example. As a result, the ease of changing the battery is less important, and sealing against moisture ingress can be improved as compared with known battery-operated fragrance sprayers.

A nozzle access for the battery-powered automatic fragrance sprayer of the type described may be included in the replacement outer casing for emitting the fragrance.

Preferably, it may be disposed on an upper third of a front face of the replacement outer casing.

Placing the nozzle access in the upper third of a front face maximises dispersal of the fragrance to a wide area, as the droplets released via the nozzle access are higher above the ground and therefore diffuse into the room more thoroughly as compared with the placement of a nozzle access on a side, top or bottom face.

At least one tuned amorphous silicon solar panel or at least one dye sensitised solar cell panel of the battery-powered automatic fragrance sprayer of the type described may be disposed in a plane substantially above or behind the nozzle access. This ensures that residual fragrance will not drip down onto the solar panel, which would reduce its ability to absorb light.

The end of the battery casing which faces a non-sprung end of the battery compartment may have a spring which is electrically connected to the battery in the battery casing.

When mounted vertically, there is a chance for the battery to over-compress the battery compartment spring and lose contact with the opposite terminal, breaking the circuit. By placing a spring at the opposing end, contact is maintained at all times between the battery and each terminal, even where the battery is mounted vertically. It also compensates for any potential variance in the length of the battery compartment during manufacturing which might otherwise affect the electrical circuit.

DESCRIPTION OF THE DRAWINGS

For a better understanding of the present invention, and to show more clearly how it may be carried into effect, reference will now be made by way of example only to the accompanying drawings, in which.

DESCRIPTION OF PREFERRED EMBODIMENTS

Figure 1:
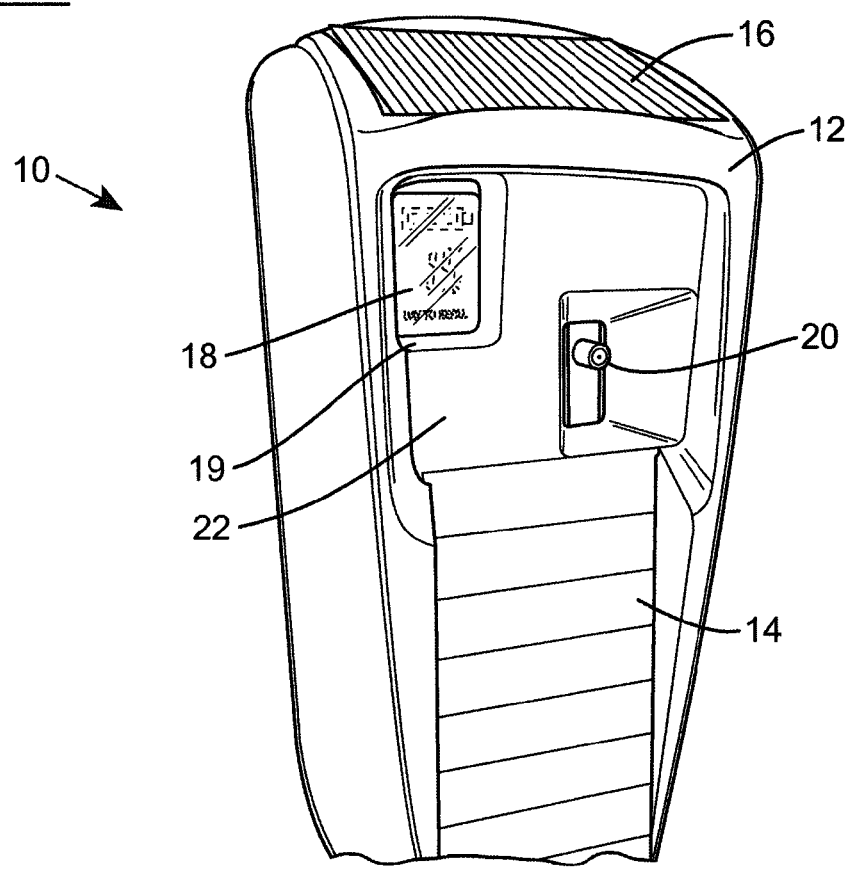
FIG. 1 shows a perspective view of a first embodiment of a kit for converting a battery-powered automatic fragrance sprayer of the type described into a solar powered automatic fragrance sprayer according to the invention.

Referring firstly to FIG. 1, a first embodiment of a kit for converting a battery-powered automatic fragrance sprayer of the type described into a solar powered automatic fragrance sprayer is generally indicated at 10. The sprayer 10 includes a replacement outer casing 12, a front-mounted solar panel 14 and a top-mounted solar panel 16 (where solar panel may in each case refer to a tuned amorphous silicon solar panel or to a dye sensitised solar cell panel), along with an LCD screen 18, an aperture 19 for the LCD screen 18, a nozzle access 20 and a front face 22.

The replacement outer casing 12 forms a substantially cuboidal box, and is adapted to be mounted to a wall. In use, the front face 22 faces away from the wall. As seen in FIG. 1, the arrangement of parts on the front face 22 has the nozzle access 20 and LCD screen 18 in the upper half of the front face 22, and the solar panels 14 and 16 are respectively disposed below and above the nozzle access 20 and LCD screen 18. The solar panel 14 is embedded into the replacement outer casing 12, and is set back from the nozzle access 20.

Contained within the replacement outer casing 12, and not shown in FIG. 1, are a controller and an actuator. The controller is adapted to activate the actuator at predetermined timed intervals, in this case about once every seven minutes. When installed, an aerosol cannister containing a fragrance is mounted within the replacement outer casing 12, and is positioned so that a valve of the aerosol cannister may be opened by the actuator, and fragrance thus expelled from the bottle is directed out of the nozzle access 20.

The replacement outer casing 12 also includes a rechargeable cell, which powers the controller and actuator, and which is charged by the solar panels 14 and 16. The LCD screen 18 shows the level of charge remaining in the rechargeable cell, as well as the time remaining until the aerosol cannister needs replacing or refilling, being viewable through the aperture 19.

The solar panels 14 and 16 are tuned amorphous silicon solar panels, of a type designed to work at high efficiency specifically with artificial light sources. The controller has a very low quiescent power consumption, and draws energy mainly upon actuation, i.e. about once every seven minutes. The battery is therefore charged from the solar panels 14 and 16 between sprays. Equally, the solar panels 14 and 16 could be dye sensitised solar cell (DSSC) panels, which, although more expensive, are also efficient at harvesting electrical energy from artificial light, and flexible enough to fit to a range of surface contours.

Tuning the panels involves optimising them to absorb artificially generated light. For example, fluorescent lighting is commonly used indoors (in public or corporate buildings) and emits light predominantly at visible wavelengths. As such, a tuned solar panel would be optimised for the absorption of photons predominantly between 400 nm and 700 nm (although other wavelengths may still be absorbed and generate useful energy), whilst non-tuned solar panels often rely on direct absorption of photons having ultraviolet wavelengths (<400 nm).

Ultraviolet photons are more energetic than photons at visible wavelengths, but are generally emitted in small quantities by lighting such as fluorescent tubing, and so the device would not be able to harvest sufficient energy to operate without utilising a tuned solar panel as above. Even other forms of lighting with different emission spectra have a common output in the visible spectrum, which is relied upon to power the device.

The actuator draws around 0.4 W of power, for around one second during actuation. In this embodiment, a 3V supply is provided, and the current draw is around 133 mA during actuation. If the sprayer is activated once every seven minutes (420 seconds), then the average current draw per second will be around 0.316 mA. If the interval is every fourteen minutes then the average current draw per second is around 0.158 mA. For an interval of every twenty-eight minutes, the average current draw per second is around 0.079 mA. The luminous flux density on the solar panel for it to provide this amount of power must be around 470 Lux, 230 Lux, or 110 Lux respectively for seven, fourteen and twenty-eight minute intervals, in order to replenish the amount of energy used in the given time period (i.e. for the level of energy harvested to exceed the level of energy used).

The luminous flux density on the solar panel is highly dependent on the environment, but typical values of the charging current from the panel in bathroom environments are 0.10-0.25 mA where an artificial strip light is the only source of illumination, 0.20-0.60 mA where there is a window on a cloudy day, and 1.0-6.0 mA where there is a window on a bright day. On average, therefore, the light in most bathrooms should be enough to support a spray frequency of once every twenty-eight minutes at the very least. Where there is a brighter light source, for example, a window or multiple artificial lights, fourteen or seven minute intervals are easily possible due to the increased luminous flux density.

A diode is provided to prevent current from flowing back from the rechargeable cell to the solar panel in dark conditions.

Figure 2:
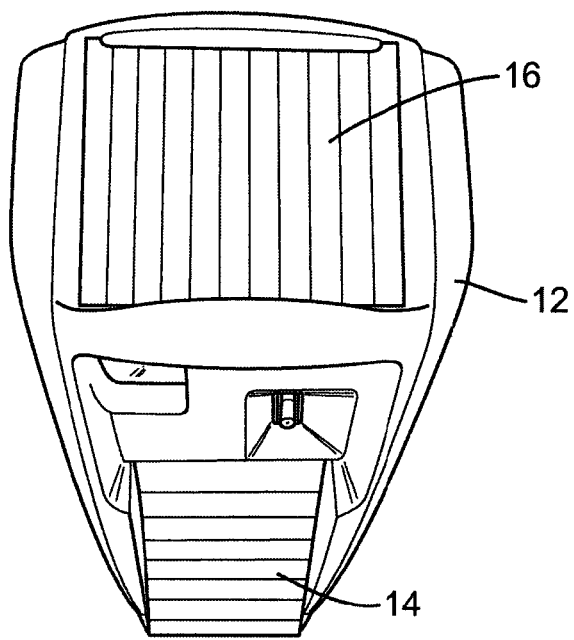
FIG. 2 shows a second perspective view of the kit in FIG. 1.

Referring now to FIG. 2, the top-mounted solar panel 16 can be seen in its entirety, mounted atop the replacement outer casing 12. The solar panel 14 can be seen to be slightly recessed from the nozzle access (20), which helps prevent residual fragrance from the nozzle access (20) from dripping onto the solar panel 14 and impairing its energy harvesting capability.

The fragrance sprayer is advantageous because it needs very infrequent maintenance. Typically, the rechargeable cell will not need changing for five to ten years. It is estimated that, over twenty years, the solar panel will lose less than 20% efficiency. The position and type of the solar panels 14 and 16 ensure that maximum energy is harvested, even from low-level artificial light.

Figure 3:
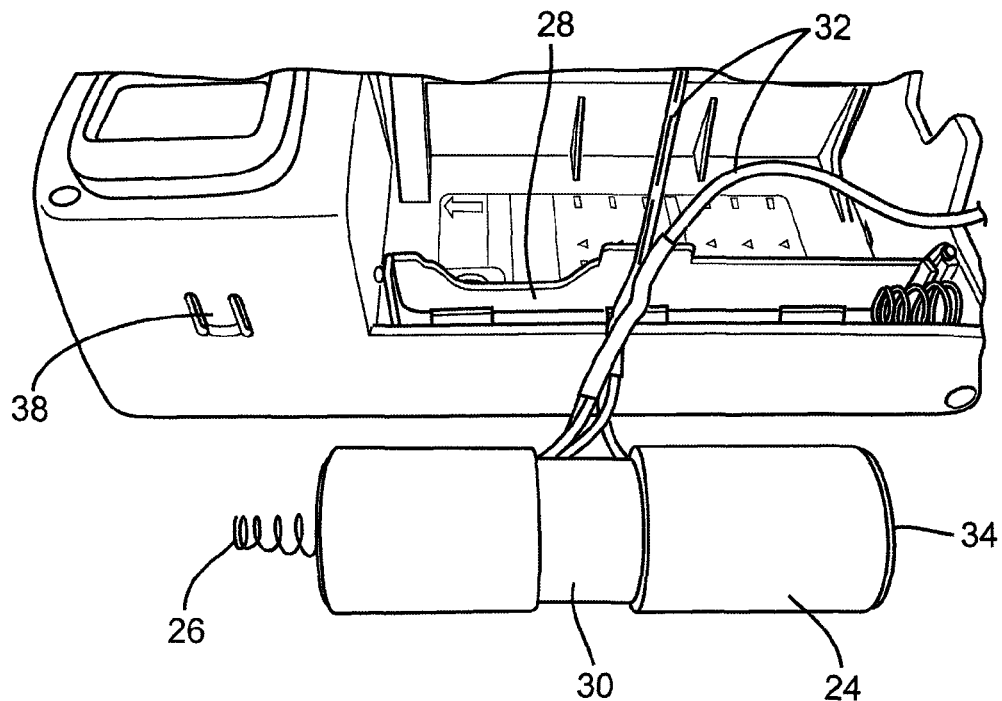
FIG. 3 shows the battery pack of the kit in FIGS. 1 and 2.

FIG. 3 depicts the battery pack 24 containing a nickel hydride low self-discharge battery 30, and having positive and negative connections areas 26 and 34, where the positive connection area is a spring. The battery compartment 28 is available to receive the battery pack 24, with cable connection means 32 electrically connecting the battery 30 to each of the solar panels (14, 16). These can then recharge the battery upon exposure to light, whether natural or artificially generated. With the battery 30 having low self-discharge, it wastes less energy and prolongs the period for which the battery can supply energy.

Figure 4:
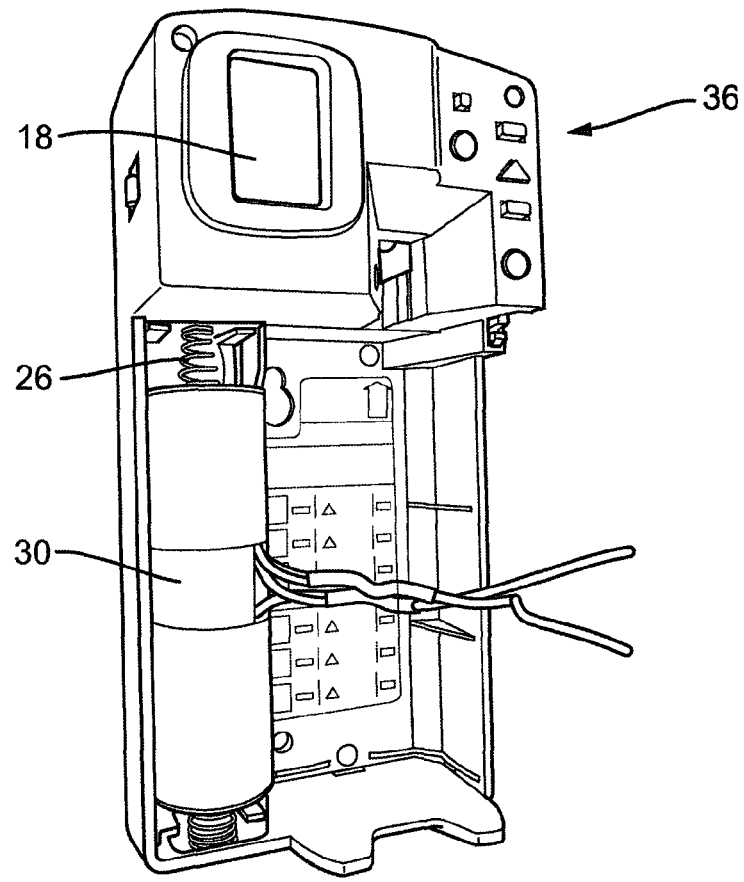
FIG. 4 shows an internal view of the controller and the battery pack mounted in the battery compartment of the kit in FIGS. 1 and 2.

FIG. 4 illustrates an internal view of a fragrance sprayer of the type described, showing the LCD screen 18 alongside the controller indicated generally at 36. These include an on/off button, a reset button, a mode button, a tone button, an adjustment button and a confirmation button, which allow the user to change the predetermined timed intervals of fragrance release, amongst other functions. The battery 30 can be seen in the battery compartment (28), with the positive connection area spring 26 clearly extended and relatively uncompressed in the battery compartment, compared to the battery compartment spring (see FIGS. 3 and 4). With the battery being mounted vertically and compressing the battery compartment spring, the positive connection area spring 26 ensures that the electrical circuit remains complete so that operation of the fragrance sprayer is not impeded.

The fragrance sprayer is typically attached to a wall in a washroom and located to optimise the current generated by incident light on the solar panel (although the wall chosen for mounting the device will have some bearing on the available luminous flux density). The unit is then relatively autonomous, with regular release of fragrance at the pre-set rate, and only needs maintenance to replace the aerosol cannister or, occasionally, the rechargeable cell.

To upgrade the unit, the old housing is removed by disengaging clips which attach to the rear unit of the fragrance sprayer at a clip 38 (with another clip in the equivalent position on the far side of the unit). The old rechargeable cell is removed with the old housing. The new rechargeable battery 30 (nickel-hydride, low self-discharge) is mounted within a casing 24 and is placed into the battery compartment 28, which can be enclosed with a cover and sealed with a watertight rubber seal. Ensuring that the cable connection means 32 is guided into the body of the device, the replacement outer casing 12 is then secured to the rear unit, again by means of the clip 38 and its twin. The whole process can be completed in a matter of seconds, streamlining the upgrade process and enabling the fragrance sprayer to function even more effectively.

The embodiments described above are provided by way of example only, and various changes and modifications will be apparent to persons skilled in the art without departing from the scope of the present invention as defined by the appended claims.

The invention claimed is:

1. A kit for converting a battery-powered fragrance sprayer into a solar powered automatic fragrance sprayer for use in an indoor lit area, comprising:
   a battery pack for fitting into a battery compartment of the fragrance sprayer, the battery pack including a rechargeable nickel-hydride (Ni-Mh) low self-discharge (LSD) battery mounted within a battery casing having positive and negative connection areas at the respective ends for connection with connectors in the battery compartment;
   a replacement outer casing for the fragrance sprayer;
   at least one tuned amorphous silicon solar panel or at least one dye sensitised solar cell panel disposed on the replacement outer casing;
   and cable connection means electrically connecting the at least one tuned amorphous silicon solar panel or the at least one dye sensitised solar cell panel to the Ni-Mh LSD battery in the battery pack.

2. A kit as claimed in claim 1, in which the total surface area of the at least one tuned amorphous silicon solar panel or the at least one dye sensitised solar cell is substantially 80 square centimeters.

3. A kit as claimed in claim 1, in which the at least one tuned amorphous silicon solar panel or the at least one dye sensitised solar cell harvests energy at a rate of substantially 5 µW per square centimeter under artificial light conditions of substantially 200 Lux.

4. A kit as claimed in claim 1, in which at least one tuned amorphous silicon solar panel or at least one dye sensitised solar cell panel is front-mounted and disposed substantially vertically when a rear wall of the fragrance sprayer is mounted to a vertical wall.

5. A kit as claimed in claim 1, in which at least one tuned amorphous silicon solar panel or at least one dye sensitised solar cell panel is top-mounted and disposed substantially between 45° and horizontal when a rear wall of the fragrance sprayer is mounted to a vertical wall.

6. A kit as claimed in claim 4, in which at least one tuned amorphous silicon solar panel or at least one dye sensitised solar cell panel is front-mounted and disposed substantially vertically when a rear wall of the fragrance sprayer is mounted to a vertical wall and at least one tuned amorphous silicon solar panel or at least one dye sensitised solar cell panel is top-mounted and disposed substantially between 45° and horizontal when a rear wall of the fragrance sprayer is mounted to a vertical wall.

7. A kit as claimed in claim 1, in which the replacement outer casing includes an aperture for an LCD screen and covers a controller.

8. A kit as claimed in claim 7, in which the aperture for the LCD screen allows the display of information relating to the energy level remaining in the battery pack.

9. A kit as claimed in claim 7, in which the aperture for the LCD screen allows the display of information relating to the amount of fragrance remaining.

10. A kit as claimed in claim 7, in which the LCD screen and controller operate on substantially 10 µA.

11. A kit as claimed in claim 1 fitted to a battery-powered fragrance sprayer, in which the fragrance sprayer includes an aerosol cannister with an actuator to release fragrance.

12. A kit as claimed in claim 11, in which the energy delivered by the battery to the actuator is substantially 0.4 Joules.

13. A kit as claimed in claim 11, in which a timer and a controller are included, the controller being adapted to activate the actuator to release fragrance at predetermined time intervals.

14. A kit as claimed in claim 13, in which the predetermined time interval is around seven minutes.

15. A kit as claimed in claim 11, in which a watertight seal is provided to protect the battery pack from moisture.

16. A kit as claimed in claim 11, in which a nozzle access is included in the replacement outer casing for emitting the fragrance.

17. A kit as claimed in claim 16, in which the nozzle access is disposed on an upper third of a front face of the replacement outer casing.

18. A kit as claimed in claim 16, in which the at least one tuned amorphous silicon solar panel or the at least one dye sensitised solar cell panel on the replacement outer casing is disposed in a plane substantially above or behind the nozzle access.

19. A kit as claimed in claim 1, in which the end of the battery casing that faces a non-sprung end of the battery compartment has a spring which is electrically connected to the battery in the battery casing.

* * * * *